(12) United States Patent
Myers et al.

(10) Patent No.: US 6,872,414 B1
(45) Date of Patent: Mar. 29, 2005

(54) ANHYDROUS LACTITOL CRYSTALS, A PRODUCT CONTAINING THE SAME AND A PROCESS FOR THE PREPARATION THEREOF AS WELL AS USE THEREOF

(75) Inventors: Craig Myers, Sabula, IA (US); Heikki Heikkila, Espoo (FI); Hannele Nikander, Espoo (FI); Juha Nurmi, Kirkkonummi (FI); Johanna Nygren, Virkkala (FI); Paula Perkkalainen, Jyvaskyla (FI); Tammy Pepper, Surrey (GB); Ilkka Pitkanen, Jyvaskyla (FI); Jussi Valkonen, Jyvaskyla (FI)

(73) Assignee: Xyrofin Oy, Kotka (FI)

( * ) Notice: Subject to any disclaimer, the term of this patent is extended or adjusted under 35 U.S.C. 154(b) by 227 days.

(21) Appl. No.: 09/666,369

(22) Filed: Sep. 20, 2000

Related U.S. Application Data

(60) Provisional application No. 60/154,853, filed on Sep. 20, 1999.

(51) Int. Cl.$^7$ .............................................. A23L 1/236
(52) U.S. Cl. ........................ 426/548; 426/658; 127/58; 424/489
(58) Field of Search ................................ 426/548, 658, 426/660; 127/58; 424/489

(56) References Cited

U.S. PATENT DOCUMENTS

| | | | |
|---|---|---|---|
| 5,478,593 | A | 12/1995 | Serpelloni et al. |
| 5,629,042 | A | 5/1997 | Serpelloni et al. |
| 5,726,303 | A | 3/1998 | Wijnman et al. |
| 5,989,352 | A | 11/1999 | Caboche |
| 6,165,511 | A | 12/2000 | Schwartz et al. |

FOREIGN PATENT DOCUMENTS

| | | |
|---|---|---|
| DE | 37 32 141 A1 | 4/1989 |
| DK | 133603 | 6/1976 |
| EP | 0 039 981 B1 | 11/1981 |
| EP | 0 231 643 A1 | 8/1987 |
| EP | 0 381 483 A1 | 8/1990 |
| EP | 0 456 636 B1 | 11/1991 |
| EP | 0 832 899 A1 | 4/1998 |
| FI | 942267 | 11/1994 |
| JP | 19674/90 | 8/1990 |
| JP | 2-255694 | 10/1990 |
| WO | WO 90/06317 | 6/1990 |
| WO | 92/16542 | 10/1992 |
| WO | 97/39739 | 10/1997 |
| WO | 98/11878 | 3/1998 |
| WO | WO 98/39350 | 9/1998 |

OTHER PUBLICATIONS

Abstract of EPO Application 832899.
Abstract of FI 942267.
Abstract of DE 3732141.
Wolfrom, M.L., et al., "Crystalline Lactositol", *J. Am. Chem. Soc.*, vol. 60: 571–573 (1938).
Velthuijsen, J.A., "Food Additives Derived from Lactose: Lactitol and Lactitol Palmitate," *J. Agric. Food Chem.*, vol. 27: 680 (1979).
Kivikoski, J., et al., "Crystal structure of lactitol (4–O–β–D–galactopyranosyl–D–glucitol) dihydrate", *Carbohydrate Research*, vol. 233: 53–59 (1992).
Halttunen, H., et al., "Influence of Drying to the Structure of Lactitol Monohydrate", *Journal of Thermal Analysis*, vol. 49: 809–816 (1997).
Yajima, K., et al., "Transformation of Lactitol Crystals and Dehydration with Grinding", *Chem. Pharm. Bull.*, vol. 45(10), 1677–1682 (1997).
Derwent Abstract of WO 97/39739.

*Primary Examiner*—Leslie Wong
(74) *Attorney, Agent, or Firm*—Scully, Scott, Murphy & Presser

(57) ABSTRACT

The invention relates to novel anhydrous (β) lactitol crystals, belonging to the orthorhombic $P2_12_12_1$ cystal system and having unit cell constants a=9.6 Å, b=11.1 Å, c=14.0 Å. The invention also relates to crystalline lactitol products containing the novel anhydrous β lactitol and to a process for the preparation thereof by crystallizing from an aqueous solution of lactitol. The novel anhydrous β lactitol is stable and nonhygroskopic and it may be used as a substitute for sugar in foodstuffs and sweets, in as well as in pharmaceutical and hygienic products.

14 Claims, 1 Drawing Sheet

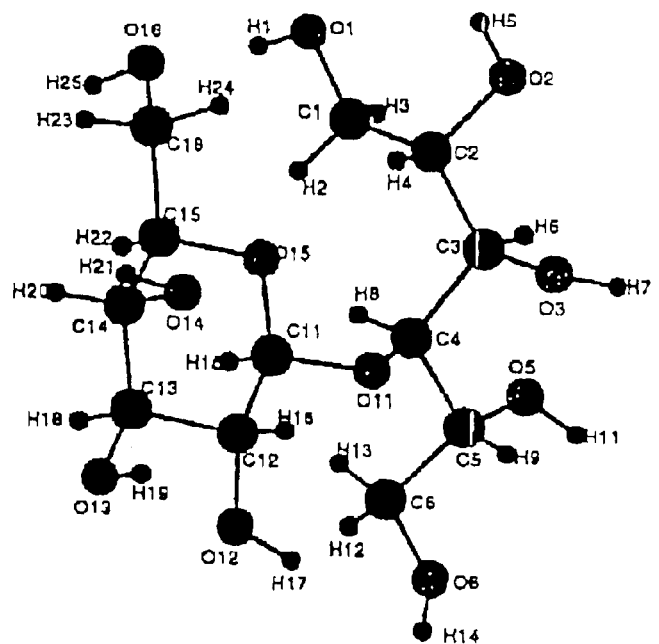
Fig. 1 β
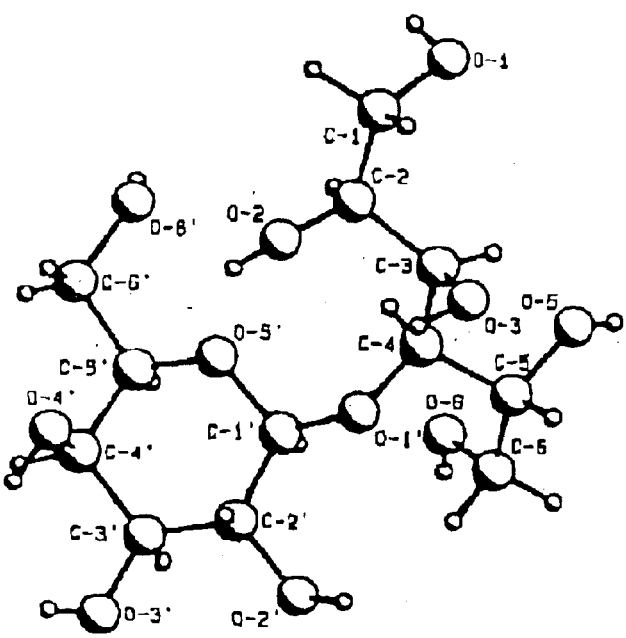
Fig. 2 α

ANHYDROUS LACTITOL CRYSTALS, A PRODUCT CONTAINING THE SAME AND A PROCESS FOR THE PREPARATION THEREOF AS WELL AS USE THEREOF

RELATED APPLICATION

This application claims priority from U.S. Provisional Application No. 60/154,853 filed Sep. 20, 1999.

The present invention relates to novel anhydrous lactitol crystals, to crystalline lactitol products containing the same and to a process for the preparation thereof and to the use thereof.

Lactitol is a special sweetener replacing saccharose; however, its energy content is only half of that of saccharose, and it does not cause an elevated blood glucose content; furthermore, it is friendly to the teeth (cf. Developments in Sweeteners, Ed. Grenby, T. H., Vol. 3, 1987, pp. 65–81).

The preparation of lactitol from lactose has long been known. Industrially lactitol is prepared analogously with the preparation of sorbitol, by hydrogenation in the presence of e.g. Raney nickel catalyst. An aqueous solution of lactose, typically having a concentration of 30% to 40% by weight on account of the low solubility of lactose, is hydrogenated at 70° C. to 130° C. at a pressure of 30 atm to 74 atm. The preparation has been described by Wolfrom et al., J. Am. Chem. Soc. 60 (1938), pp. 571–573.

In accordance with the above-stated reference (Wolfrom et al., 1938), "lactitol anhydride" could be crystallized by adding ethanol to a lactitol solution evaporated to a high concentration. After a crystallization time of one month (from anhydrous ethanol), the lactitol yield was 80%; the product was recrystallized from a water-ethanol solution in an ice bath. The resultant "lactitol anhydride" was a highly hygroscopic substance. The crystal form was tetrahedric, the melting point was 144° C. to 146° C. and the specific rotation in water +14° (4 g/100 ml, 23° C.).

Int J. Am. Chem. Soc. 74 (1952), p. 1105, Wolfrom et al. state that the above "lactitol anhydride" is metastable, since in renewed tests carried out at two different laboratories only dihydrate was crystallized, having a melting point of 72.5° C. to 74° C. The anhydrous product disclosed by Wolfrom et al. (1938) was thus an impure dihydrate and not crystalline anhydrous lactitol.

Lactitol hydrate powders anhydrated to a water content below 3% have been prepared by drying both a lactitol solution and crystalline hydrate. The hygroscopicity of these powders is made use of in the drying of moist mixtures (European Patent Application No. 0231643, 1986).

Japanese Patent Application No. 64-19452 (1989) discloses a solid lactitol product which is called "lactitol anhydride" and which is prepared by drying crystalline lactitol monohydrate. The product is hygroscopic and has a melting point of 121° C. to 123° C. This product is instable and has been named A or A1 anhydrous lactitol in the literature. EP Patent 39981 describes the crystallization of lactitol to form a product melting at about 121–123° C. Although stated in the patent to be lactitol monohydrate, it appears that this product is in reality a hydrate mixture containing a substantial portion of anhydrous lactitol. The production of an anhydrous lactitol having a melting point of about 120° C. by drying of lactitol monohydrate has been described also in Halttunen et al., J. Thermal Anal. 49, 1997, 809–816.

A different anhydrous lactitol may be crystallized from an aqueous solution as described in WO 92116542, incorporated herein by reference. The process comprises cooling or evaporating a supersaturated lactitol solution at a temperature above 70° C. to provide anhydrous lactitol having a melting range of 149–152° C. The anhydrous lactitol has a monoclinic crystal structure and a low hygroscopicity. This anhydrous lactitol crystal form has also been called B or A2 anhydrous lactitol in the literature. It will herein be called α lactitol, as it was the first known crystal structure of anhydrous lactitol. Its unit cell dimensions are a=7.614 Å, b=10.757 Å, c=9.370 Å and V=729.0 Å$^3$ as indicated in Kivikoski et al., Carbohydrate Research, 223 (1992) 45–51. The α lactitol has a melting enthalpy of about 149 J/g and it is considered to be a very stable anhydrous lactitol form.

The two anhydrous lactitol forms and their different behaviors are discussed also by Koichi Yiajima et al in Chem. Pharm. Bull, 45(10) 1677–1682 (1997). In the present description and claims the anhydrous lactitol melting at about 121–123° C. will be called A1 and the monoclinic anhydrous lactitol (A2) melting at about 149–152° C. will be called α lactitol.

The production of a crystalline anhydrous lactitol composition having a melting point of about 151° C. and a melting enthalpy higher than about 135 J/g is described in EP 0832899 A1. This lactitol composition comprises a different physical form of anhydrous lactitol in that it has a porous alveolar structure.

In addition to the anhydrous form crystalline lactitol has been reported to occur in the form of monohydrate, dihydrate and trihydrate. Among these crystal forms of lactitol, lactitol monohydrate and anhydrous lactitol are of great commercial interest e.g. on account of their low hygroscopicity.

The way in which the different crystalline lactitol forms can be crystallized separately from each other in pure form is described in WO 98/39350. The crystallization of the pure lactitol forms is based on the solubility curves defined for each crystalline species. The anhydrous lactitol form which is crystallized by the process of said publication is the monoclinic α form.

SUMMARY OF THE INVENTION

The present invention is based on the finding that lactitol is capable of crystallizing in a new anhydrous crystal structure which is distinct from the two earlier known anhydrous forms. The crystal shape (morphology) is typically elongated. The crystal shape may be affected by the actual crystallization conditions and by other components in the feed liquid. The shape is often more or less needle-like. The crystals belong to the orthorhombic crystal system. In contrast to this, the A1 form has been found to be difficult to crystallize in pure form from aqueous solutions although it seems to crystallize with the crystalline hydrate forms giving a distinct peak around 121–123° C. in the DSC curves of impure hydrate forms such as those produced according to the above mentioned EP Patent 39981. The α lactitol form is more stable than the A1 form and is the crystal form so far predominantly crystallized from aqueous solutions above 70° C. Its crystal form is monoclinic and the crystals are typically square-like in shape.

The novel anhydrous lactitol crystal is called β (or A3) throughout this description for ease of distinguishing it from the prior known anhydrous lactitol crystals, α (A2) and A1.

The novel crystals, their mixtures, production and use according to the present invention are defined in the appended claims.

BRIEF DESCRIPTION OF THE DRAWINGS

FIG. 1 is a simulation projection formula of novel anhydrous lactitol crystal β.

FIG. 2 is a projection formula of prior known monoclinic anhydrous lactitol α.

DETAILED DESCRIPTION OF THE INVENTION

The novel anhydrous lactitol crystal (B) of the present invention belongs to the orthorhombic $P2_12_12_1$ crystal system and it has been found to have the unit cell constants of about a=9.6 Å, b=11.1 Å, c=14.0. Measurements made on several samples indicate for the cell constants an average of a 9.622 Å, b=11.132 Å, c=14.022 Å. A simulated projection formula of the molecule is shown in FIG. 1 while FIG. 2 shows the projection formula of the prior known monoclinic anhydrous lactitol α. The pure β crystal has a melting point of 151° C. (onset) to 152.5° C. (peak) measured by DSC (Differential Scanning Calorimetry) at a heating rate of 2° C./min, it has a water content below 0.5% and a lactitol content of more than 99%. The cell units have been measured by single crystal x-ray measurement and by a powder diffraction measurement using a Pirum analysis.

The unit cell constants presented above should not be taken to be absolutely correct. Thus, as persons skilled in the art will understand, the unit cell dimensions of any crystal structure vary within certain accepted limits and the identical measurement is hardly ever obtained for two different single crystals or powder diffractograms. A normal variation in the cell unit dimensions is thus implied herein. The volume of the unit cell of the β lactitol is about 1502 $Å^3$.

The orthorhombic anhydrous β lactitol crystals have been measured to show a very low hygroscopicity and it has been found that the anhydrous β crystals have a very low lactulitol content. Lactulitol is a common impurity in hydrogenated lactitol syrups. The amount of lactulitol found in the anhydrous β crystals is typically below 0.5% and most often below 0.1% on the dry substance, even when lactulitol is present in the feed liquid.

The novel β lactitol crystals have also been observed to have a low content of coloured impurities. Thus, the β lactitol can provide a very pure product in industrial production. Because of its low water content and low hygroscopicity the β lactitol is easy to dry in industrial processes.

Depending on the crystallization procedure the orthorhombic anhydrous β lactitol may have as impurities monoclinic anhydrous α lactitol and also a slight amount of lactitol monohydrate. It is also possible to produce a mixture of the anhydrous β and anhydrous α and/or lactitol monohydrate. Such mixed products form part of the present invention.

Samples of the orthorhombic anhydrous β lactitol crystals of the present invention have been found to have a melting enthalpy of about 165–170 J/g, more typically 166–169 J/g. In contrast thereto the prior known crystalline monoclinic anhydrous lactitol α form has a melting enthalpy of about 149 $\mu$g. The β crystals are stable and hard and are not appreciably affected by milling. The melting enthalpy of a sample of β lactitol crystals was reduced to about 160–165 J/g, more typically to 161–163 J/g by milling, although the β form was not found to have changed into the α form.

It should be noted that the above mentioned values for melting point and melting enthalpy for the novel anhydrous lactitol crystals should not be considered as limiting the invention since the melting point and melting enthalpy may vary somewhat depending on the structural and chemical purity level of the sample.

There are various ways of producing the novel orthorhombic anhydrous β lactitol. Specifically the crystals can be produced by crystallization from aqueous solutions of lactitol either by boiling (evaporative) crystallization or by cooling crystallization or by a combination of the two. The appended claims define the preferred ways of producing β lactitol by crystallization. The contents of said claims are included herein by reference.

Thus, the orthorhombic anhydrous β lactitol crystals may be produced by any boiling and/or cooling crystallization processes at a temperature between about 70 and 150° C. which typically produce the α form of anhydrous lactitol as a first crystal yield, provided that the first obtained crystal yield is conditioned in the solution at a temperature of about 70–100° C. for a sufficient time to allow the first crystal yield to convert into a second crystal yield comprising orthorhombic anhydrous lactitol β crystals.

The term "conditioning" as used in this specification and the appended claims is intended to mean that the crystal yield is allowed a sufficient time under suitable conditions for the crystals to take the orthorhombic anhydrous shape of β.

It seems that under normal crystallization conditions, such as those described in the same applicant's earlier application (WO 92/16542) the crystal form of the anhydrous crystals is that of α. However, a conditioning in the solution either after the actual crystallization or during the crystallization itself will make the monoclinic α crystals change into the orthorhombic β form. The change is gradual and will become more complete with time. Thus, a conditioning of one hour may be sufficient in certain conditions while in some cases, and especially if a complete change into the β form is desired, the conditioning may last for days or even weeks. Under industrial conditions a conditioning exceeding one day is not considered practical and a wet conditioning of about 2 to 5 hours will also be sufficient in most cases.

Thus, the typical square shaped monoclinic anhydrous α lactitol crystals will, when maintained in the solution at a temperature at or above about 70 to 80° C., preferably closer to 70° C., slowly change into the typical elongated orthorhombic anhydrous β lactitol crystals. This is so even though the solution may have been seeded with seed crystals of the α form. Although applicants do not wish to be bound by any theory, this seems to indicate that the β crystals have the more stable crystal form of the two at the crystallization conditions.

The time required for the change from monoclinic anhydrous lactitol α to orthorhombic anhydrous lactitol β depends on many factors such as the temperature, the impurities in the solution, the supersaturation of the solution, etc. Normally the change begins within one or more days, while a total change may require up to two or three weeks to be complete. Mixing of the solution during crystallization also improves the yield of β lactitol.

The orthorhombic anhydrous lactitol β may also be crystallized directly from supersaturated aqueous solutions of lactitol either by boiling or cooling crystallization, provided that the crystallization is seeded with seed crystals of β. In such a case the crystal form of the initial crystal yield will comprise orthorhombic anhydrous lactitol β and no conditioning is needed to obtain β crystals.

In a preferred embodiment of the direct crystallization of orthorhombic anhydrous β lactitol a combination of boiling and cooling crystallization is performed, wherein a boiling crystallization is first performed while using seeds of β crystals, and after the boiling crystallization a cooling crystallization is performed down to about 70° C. to optimize the crystal yield. It has been found that the end temperature of the crystallization may even drop slightly below 70° C., such as to about 68° C. without any undue amount of lactitol monohydrate being formed, especially if the cooling at the end is fairly rapid. However, no conditioning should be performed below 70° C., since in such a case contamination by lactitol monohydrate is very likely to happen.

The β seeds used for the seeding may comprise milled and/or sieved crystals or, in a preferred embodiment a so called crystal foot of β crystals is produced by providing a large amount of β crystals in a solution by a pre-crystallization step. The crystal mass is preferably conditioned so as to make sure that the crystal form in the crystal foot is the desired β lactitol.

The novel orthorhombic anhydrous lactitol β of the present invention may also be crystallized directly from an aqueous solution by boiling and/or cooling crystallizations in which the crystallization is slow, i.e. a boiling crystallization wherein there is a low input of energy or a cooling crystallization wherein the cooling time is long compared to normal industrial crystallization times used in the production of anhydrous lactitol α. Such a crystallization may even take two days or more in order to provide a crystal yield which consists essentially of β crystals. However, β crystals have also been observed under suitable conditions in much shorter crystallization times. A shorter crystallization may require the use of accelerating means or the above mentioned conditioning time in order to provide a meaningful yield of β. The aqueous lactitol solution may be seeded or allowed to seed spontaneously.

It has been found that the crystallization of the orthorhombic anhydrous lactitol β is accelerated and/or improved by the addition of impurities such as lactulitol to the aqueous solution of lactitol. With an increased lactulitol content in the solution the crystallization time may be significantly lowered. Under suitable conditions β crystals have been observed to form in a very short time such as under one hour. Effective mixing or agitation seems to improve the yield.

According to a preferred crystallization method, the lactitol solution is evaporated under stirring at a temperature of 80° C. to 100° C. to a suitable supersaturation, seed crystals are added if desired, and the evaporation is continued, advantageously with addition of solution, to increase the crystal concentration to a dry solids content of about 90% by weight. Thereafter the crystals can be conditioned if they are square shaped anhydrous ca crystals or just separated and dried if they are typical elongated anhydrous β crystals. However, it is generally advantageous to continue the crystallization by cooling the mixture first at a slow rate and ultimately at a faster rate to a temperature of 70° C. to 90° C. until the crystallization yield is appropriate, typically 40% to 60%, whereupon the crystals are wet conditioned if needed, separated or, if necessary, washed and dried.

Dried crystals are typically obtained at a yield of 30% to 50%, and the purity of the crystals is typically more than 99% and the water content typically below 0.5%. Conventional evaporating and cooling crystallizers, centrifuges, and driers of the sugar industry may be used in the preparation.

The crystalline orthorhombic anhydrous lactitol β of the invention has been found to have a very low hygroscopicity both at 25° C. and 60% relative humidity and at 40° C. and 75% relative humidity. The water sorption of a sample of β crystals was less than about 0.3% of water in 45 days even when the relative humidity of the ambient air was 75% at 40° C.

The novel crystalline orthorhombic anhydrous lactitol β is distinct from the prior known anhydrous crystalline lactitol forms A1 and α. It is also distinct from the other known crystalline lactitol forms. Table 1 below indicates the various known characteristic data of the crystalline lactitol forms.

TABLE 1

| | Anhydrous β | Anhydrous α | Monohydrate | Dihydrate | Trihydrate |
|---|---|---|---|---|---|
| Molecular weight | 344.3 | 344.3 | 362.3 | 380.3 | 398.4 |
| Crystal system | orthorhombic | monoclinic | orthorhombic | tetragonal | ortho rhombic |
| spatial group | $P2_12_12_1$ | $P2_1$ | $P2_12_12_1$ | $P4_12_12_1$ | $P2_12_12_1$ |

The novel β lactitol crystals seem to be very stable and they have been found to be harder than the α crystals. These two stable anhydrous lactitol crystal forms can easily be distinguished from each other by their different crystal structures as determined by x-ray powder diffraction. They can also be distinguished by their different melting enthalpies (α: 149 J/g; β: 166–169 J/g). However, their melting points are so close to each other that a melting point analysis alone cannot distinguish β from α.

In connection with this invention, the term crystalline signifies the fact that the product is crystalline in the technical sense (Integral crystal structure) and not powdery (microcrystalline). The mean crystal size of the industrially manufactured product is preferably between 0.2 mm and 0.6 mm depending on the application, and the desired size is obtained when the seeding technique of the invention is employed in the crystallization. The crystal size is not limited to below 1 mm as crystals above 2 mm have also been obtained and the crystal size is only dependent on the crystallization conditions.

The new crystalline orthorhombic anhydrous lactitol β has a good flowability and storability, since it is stable at room temperatures, the relative humidity being below 60%.

On account of its excellent technical and physiological properties, the new crystalline orthorhombic anhydrous lactitol β is particularly suitable as a substitute for sugar in foodstuffs and sweets. By combining the new lactitol with other sweeteners, such as saccharine or xylitol or other lactitol forms such as lactitol monohydrate or anhydrous lactitol α, a sweetener resembling sugar and yet having a considerably lower energy content. Such a sweetener is friendly to the teeth. It can be used instead of sugar for instance in sweets, jams, bakery products, chocolate, juices, cream fillings and ice-creams, as well as in pharmaceutical and hygienic products, such as laxative and toothpaste. The new anhydrous lactitol can also be used for tabletting purposes.

The new anhydrous lactitol β also is particularly suitable for the production of chocolate, to which it is considerably better suited than lactitol monohydrate and lactitol dihydrate and anhydrides prepared therefrom by drying.

The new anhydrous lactitol β can be milled for various applications wherein smaller particle sizes are required. Milling lowers the melting point of the product to about 145–149° C. and the melting enthalpy to about 160–165 µg, typically 161–163 J/g. While not wishing to be bound by any theories, the change in characteristics is believed to be due to a certain formation of amorphous components at milling. The milling may produce particles having a mean particle size between about 5 and 300 µm, preferably between 50 and 200 µm.

The following example illustrate the invention.

Example 1

Boiling and Cooling Crystallization, Spontaneous Seeding 12 kg of lactitol monohydrate having 99% of lactitol on dry solids was dissolved in water to give a solution of about 50% by weight. A quantity of the solution was transferred into an evaporator (20 l rotating evaporator), and the temperature was raised to 80° C. The solution was evaporated under simultaneous agitation, whereupon lactitol crystals seeded spontaneously at about 80° C. The intake of more feed solution into the evaporator was started and the evaporation was continued until the dry solids content was 92.6% by weight.

The resultant mixture containing square shaped anhydrous lactitol α crystals was transferred into a 10 l cooling crystallizer having a temperature of 92° C. After stirring of about one hour, the mixture was cooled in a controlled manner [T=92° C. 14(t/18)$^{2°}$ C., wherein T is the temperature and t the time elapsed (hours)]. The crystallization was terminated after cooling of 18 hours at 78° C., at which point the dry solids content of the mother liquor was 83.2% by weight, in other words, the crystal yield of anhydrous α was about 60%.

The crystals were retained in the solution and the solution was kept at 76° C. for 44 hours. During this time the square shaped anhydrous α crystals changed into typical needle-like anhydrous β crystals. The needle-like crystals were separated from the mother liquor with a conventional centrifuge (diameter of basket 0.4 m); the centrifuging was carried out for three minutes at a speed of rotation of 1800 rpm. The crystals were washed with 0.5 l of warm water at a speed of rotation of about 1000 rpm. Finally, the crystals were dried with a conventional drum drier with hot air (90° C.).

4.3 kg of dried anhydrous β crystals was obtained (yield about 46%); the crystal size was about 0.5 mm, the melting point was 150–152° C., the lactitol content was about 99.5%, the water content was about 0.01%.

Example 2
Cooling Crystallization, Seeding with α Lactitol

A lactitol solution containing 99.5% of lactitol on dry solids was evaporated to a supersaturation of about 1.15 and transferred into a cooling crystallizer. The crystallizer was a conventional horizontal cylindrical batch-operated cooling crystallizer provided with a mixer and a recycling water jacket whose temperature was controlled by means of a microprocessor.

The cooling crystallization was performed in 10 hours from 82° C. to 70° C. with seeding with anhydrous α crystals. At the end of the cooling the crystal yield was composed of square shaped anhydrous α crystals. The crystals were retained in the solution at about 70° C. for 38 hours at the end of which the square shaped crystals had changed into typical needle-like crystals of anhydrous β.

The crystals were centrifuged off, washed rapidly with water, and dried with a fluidization drier with air having a temperature of about 65° C. Dried anhydrous β crystals were obtained at a yield of about 30%; the crystal size was about 0.45 mm, the melting point 151° C. to 152° C. and the water content 0.2%.

Example 3
Cooling Crystallization Under Varying Conditions

A series of four solution purities with 100%, 99%, 98% and 95% lactitol at two different cooling rates 80° C. to 70° C. during 44 hours and during 2 hours, respectively, were tested at low supersaturation (about 1.02) and high supersaturation (about 1.30) and different contents of lactulitol.

The lactitol used was lactitol monohydrate produced by Xyrofin Oy, Kotka, Finland and the lactulitol was crystalline lactulitol with a purity of 91% produced in the laboratory by Xyrofin Oy, Kantvik, Finland.

About 1 kg of water was heated to 75° C. and 2.1 kg of the lactitol monohydrate was dissolved in the water. For the lactulitol tests to provide a 0.5% lactulitol solution 10 g of lactulitol was added to the solution and to provide a 1.5% lactulitol solution 35 g of lactulitol was added to the base solution. Then the solution was evaporated at 80° C. to the set supersaturation values.

The evaporated solutions were each divided into two reaction vessels which were heated to 82° C. The solutions were stirred for 10–20 minutes to reach the seeding temperature. Where appropriate the solutions were seeded with 1 g milled monoclinic anhydrous lactitol α (lot N050 32701 manufactured by Xyrofin Oy, Kotka). One lot was seeded with milled β crystals. Then the cooling programs were started: 80° C.->70° C. during 2 h and 80° C.->70° C. during 44 h, respectively.

After the cooling half of the mass was centrifuged. Centrifugation was made using a laboratory centrifuge (24 cm basket). The basket of the centrifuge was warmed to 80° C. before use. Centrifugation parameters were 3500 rpm, 1 minute and 15 ml or 5 ml hot wash water. The crystal cake was dried at 80° C. oven for an hour.

Crystallization conditions and appearances of needle-like β crystals are presented in Table 2.

TABLE 2

Crystallization conditions and the appearance of needle-like crystals

| Lactitol | Lactulitol | Seeding | Cooling | Cooling | Seeding & | Appearance of needle crystals | | | |
|---|---|---|---|---|---|---|---|---|---|
| % | % | ss | ° C. | time h | seed | 5 h | 20 h | 40 h | 60 h |
| 99.9 | — | 0.99 | 84->70 | 3 | N050 | – | – | – | + |
| 99.9 | — | 1.03 | 83->70 | 49 | N050 | – | – | – | – |
| 99.8 | — | 1.15 | 83->70 | 2 | Spontaneous & N050 | – | – | 50 h+ | + |
| 99.8 | — | 1.13 | 82->70 | 44 | N050 | – | – | | |
| 98.9 | 0.5 | 1.00 | 82->70 | 5 | N050 | – | – | – | 92 h+ |
| 98.9 | 0.5 | 1.01 | 82->76 | 48 | N050 | – | – | – | 166 h+ |
| 98.7 | 0.7 | 1.21 | 80->70 | 2 | N050 | – | + | + | + |
| 98.7 | 0.7 | 1.20 | 82->70 | 44 | N050 | – | – | 49 h | + |
| 98.0 | 1.4 | 1.03 | 80->70 | 2 | Spontaneous & N050 | + | + | + | + |
| 98.0 | 1.4 | 1.00 | 80->70 | 44 | N050 | | + | + | + |
| 98.1 | 1.5 | 1.29 | 80->70 | 2 | Spontaneous | – | | + | + |

TABLE 2-continued

Crystallization conditions and the appearance of needle-like crystals

| Lactitol % | Lactulitol % | Seeding ss | Cooling °C | Cooling time h | Seeding & seed | Appearance of needle crystals 5 h | 20 h | 40 h | 60 h |
|---|---|---|---|---|---|---|---|---|---|
| 98.1 | 1.5 | 1.29 | 80->70 | 44 | Spontaneous | + |  | + | + |
| 95.7 | 0.3 | 1.09 | 81->70 | 44 | N050 | − | + | + | + |
| 95.7 | 0.3 | 1.09 | 81->70 | 44 | Needle | + | + |  |  |
| 99.1 | 0.5 | 0.97 | 93->80 | 44 | No |  | 24 h | + | + |
| 99.1 | 0.5 | 0.97 | 93->80 | 44 | N050 | − | − | + | + |
| 98.9 | 0.6 | 1.43 | 78->70* | 44 | No | − | + | + | + |
| 98.9 | 0.6 | 1.23 | 77->70* | 44 | N050 |  | + | + | + |

After the cooling program had stopped half of the mass was centrifuged and dried. Some crystals were dried at 80° C. for 10 minutes and then placed in a room temperature climate cabin where the relative humidity was controlled to be under 10%. Change in weight was recorded for a day. Crystals crystallized from lower purity solutions showed a smaller change in weight than crystals crystallized from higher purity solutions.

Example 4
Crystallization, Seeding with β Crystals

A crystallization was performed in a pilot plant 400-1 crystallizer as boiling and cooling crystallization. Lactitol run-off from a previous lactitol crystallization (purity 94% on DS; 0.6% lactulitol) was used as free solution.

The lactitol run-off was filtered (1 μm GAF) and used as feed solution. The solution was evaporated to RDS 86–87% at a temperature of 67–74° C. during 3.5 hours. Thereafter seeding (150 g) was made by milled anhydrous β lactitol seed crystals at a temperature of 80° C. (supersaturation s=1.10). Boiling was continued for 2 hours (final Brix 89). The resulting crystals were seen to have the characteristic needle-like form of β.

The mass was then dropped into a 400 l cooling crystallizer. The cooling program was (82° C.->70° C., 15 h, exp. 1=0.75° C./h). The resulting crystals were typical needle-like in shape indicating the production of anhydrous lactitol β.

After cooling the mass was left at a constant temperature (about 70° C.) for 75 hours for ascertaining whether the β crystal yield was stable. No change in the crystal form was detected.

Thereafter the crystals were centrifuged (2100 rpm, 3 minutes, 3*3 s warm washing water, basket diameter 0.4 m). The crystals were dried in a drum dryer at 95° C. About 50 kg of crystals were obtained (DS yield 20%).

The crystals were analysed and were found to be β crystals. The crystals were milled, sieved and used in the application tests of Examples 5 to 7.

Example 5
Seeding with β Crystals

The crystallization was performed in a pilot plant 400-1 crystallizer as boiling and cooling crystallization. Lactitol run-off from a previous lactitol crystallization (purity 96% on DS; 0.5% lactulitol) was used as feed solution.

The lactitol run-off was filtered (1 μm GAF) and used as feed solution. The solution was evaporated to RDS 86–87% at a temperature of 70–80° C. during 3.5 hours. Thereafter seeding (340 g; 0.09% on DS) was made by milled and sieved anhydrous β lactitol seed crystals at a temperature of 80° C. (supersaturation s=1.19). Boiling was continued for 4 hours (final Brix 89). Most of the resulting crystals were seen to have the characteristic elongated form of β crystals, but also some square shaped at crystals were seen during boiling. A centrifuged sample of boiling end mass was analysed to contain detectable amounts of the α form.

The mass was then dropped into a 400 l, cooling crystallizer. The cooling program was (81° C.->70° C., 16 h, linear). After cooling the mass was left at constant temperature (about 70° C.) for 8 hours after which a crystal sample was taken for analysis. The crystals were found to be β crystals.

Conditioning at about 70° C. was continued for 20 hours for ascertaining that the β crystal yield was stable. No change in the crystal form was detected.

Thereafter the crystals were centrifuged (2100 rpm, 5 minutes, 3*3 s warm washing water, basket diameter 0.4 m). The crystals were dried in a drum dryer at about 95° C.

Example 6
Production of a β Crystal Foot

The preparation of a crystal foot was performed in a pilot-plant 10-1 crystallizer as cooling crystallization. Lactitol run-off from a previous lactitol crystallization (purity 96% on DS; 0.5% lactulitol) was used as feed solution. The solution was evaporated to RDS about 86% at a temperature of about 80° C. The solution was transferred into the crystallizer and seeded by milled and sieved anhydrous β lactitol seed crystals (100 g, 0,48% on DS) at a temperature of 84° C. (supersaturation s=1.03).

The cooling program was (84° C.->70° C., 16 h, linear). After cooling the mass was left at a constant temperature (about 70° C.) for 54 hours after which a crystal sample was taken for analysis. The crystals were found to be β crystals.

Conditioning at about 70° C. was still continued for 120 hours. No change in the crystal form was detected. An about 30% dry substance yield was obtained.

Example 7
Seeding with a β Form Crystal Foot

A crystallization was performed in a pilot plant 400 liter crystallizer as boiling and cooling crystallization. Lactitol run-off from a previous lactitol crystallization (purity 96% on DS; 0.5% lactulitol) was used as feed solution.

The lactitol run-off was filtered (5 μm GAF) and used as feed solution. The solution was evaporated to RDS 85–86% at a temperature of about 80° C. during 3.5 hours. Thereafter seeding was made by β form crystal foot (about 0.4% on DS) at a temperature of about 80° C. (supersaturation s=1.13).

Boiling was continued for 3 hours (final Brix 89). Most of the resulting crystals were seen to have the characteristic needle-like form of β, but also some square shaped α crystals were seen during boiling.

The mass was then dropped into a 400 liter cooling crystallizer. The cooling program was (85° C.->70° C., 16 h, linear). After cooling the mass was left at constant temperature (about 70° C.) for 8 hours after which a crystal sample was taken for analysis. The crystals were found to be β crystals, a detectable amount of α form crystals was present.

Example 8
Seeding with β Form Crystals at High Temperature

A crystallization was performed in a pilot plant 400 liter crystallizer as boiling and cooling crystallization. Lactitol run-off from a previous lactitol crystallization (purity 96% on DS; 0.5% lactulitol) was used as feed solution.

The lactitol run-off was filtered (5 μm GAF) and used as feed solution. The solution was evaporated to RDS 88–89% at a temperature of about 80–90° C. during 2 hours. Thereafter seeding was made by β form crystal foot (about 2.5% on DS) at a temperature of about 90° C. (supersaturation s=1.10).

The crystal foot was made as described in Example 6, except that seeding was made at 90° C. and the cooling program was as follows: 90° C.->80° C., 16 h, linear.

Boiling was continued for 3 hours (final Brix 90). Most of the resulting crystals were seen to have the characteristic needle-like form of β, but also some square shaped α crystals were seen during boiling.

The mass was then dropped into a 400 l cooling crystallizer. The cooling program was (92° C.->80° C., 16 h, linear). After cooling the resulting crystals were seen to have the characteristic needle-like form of β lactitol.

Example 9
Seeding with a β Form Crystal Foot, Pure Cooling Crystallization

A crystallization was performed in a pilot plant 6 liter crystallizer as cooling crystallization.

Lactitol run-off from a previous lactitol crystallization (purity 96% on DS; 0.5% lactulitol) was used as feed solution.

The lactitol run-off was filtered (5 μm GAF) and used as feed solution. The solution was evaporated to RDS 87–88% at a temperature of about 80° C. during 3 hours. Thereafter seeding was made by β form crystal foot (about 2% on DS) at a temperature of about 86° C.

The crystal foot was made as described in example 8.

The cooling program was (86° C.->70° C., 16 h, linear). After cooling the resulting crystals were seen to have the characteristic needle-like form of β lactitol.

Example 10
Spontaneous Seeding at High Temperature

A crystallization was performed in a pilot plant boiling pan and a 2 liter reaction vessel. Lactitol run-off from a previous lactitol crystallization (purity 96% on DS; 0.5% lactulitol) was used as feed solution.

The lactitol run-off was filtered (1 μg GAF) and used as feed solution. The solution was evaporated in a boiling pan to RDS about 88% at a temperature of about 95° C. Spontaneous square shaped α form crystals were observed. The boiling was continued for about 40 minutes, after which part of the mass was transferred into 2-l reaction vessel at a temperature of 95° C.

The cooling program was (95° C.->85° C., 16 h, linear). After cooling the mass was left at constant temperature (about 85° C.) and the conversion from α form crystals to β form crystals was observed. After 10 days conditioning only α form crystals were seen. After 11 days conditioning also some β form crystals were seen and after 14 days the crystal yield was totally in the β lactitol form.

Example 11
Seeding with α Crystals, Subsequent Conditioning to β Form

A crystallizations were performed in a pilot plant 400 liter, in a 10 liter and a 6 liter crystallizer as boiling and cooling crystallizations. Lactitol run-off from a previous lactitol crystallization (purity 96% on DS; 0.5% lactulitol) was used as feed solution.

The lactitol run-off was filtered. (1 μm GAF) and used as feed solution. The solution was evaporated to RDS 86–87% at a temperature of 70–80° C. during 2 hours. Thereafter seeding (75 g; 0.025% on DS) was made by milled and sieved anhydrous α lactitol seed crystals (lot NO50T9C16 produced at Thomson, USA) at a temperature of 80° C. Boiling was continued for 3.5 hours (final Brix about 91). The crystals were seen to have the square shaped form of α crystals.

The mass was then transferred into 400-l, 10–l and 6-l cooling crystallizers.

The cooling program in the 400-l crystallizer was (84° C.->70° C., 16 h, exp. 1). After cooling the mass was left at constant temperature (about 70° C.) and the conversion from α form crystals to β form crystals was observed. After 3 days conditioning the crystals were still in the α form. After 6 days conditioning the crystal mass was totally in β form.

The cooling program in the 6-l crystallizer was (84° C.->70° C., 16 h, exp. 1). After cooling the mass was left at constant temperature (about 70° C.) and the conversion from α form crystals to β form crystals was observed. One day from the start of the cooling program the crystals were still α form. Two days after the start of the cooling program also needle-like β form crystals were present in the mass and after three days the crystal mass was totally in β form.

The cooling program in the 10-l crystallizer was (84° C.->70° C., 75 h, exp. 3). After cooling the mass was left at constant temperature (about 70° C.) and the conversion from α form crystals to β form crystals was observed. One day from the start of the cooling program the crystals were still α form. Two days after the start of cooling program also needle-like β form crystals were present in the mass and after three days the crystal mass was totally in β lactitol form.

The faster conversion speed in the 6-l and 10-l crystallizers is evidently due to higher mixing speed compared to the 400-l crystallizer.

Example 12
Milling Of Anhydrous β Lactitol

Good quality anhydrous β lactitol crystals (lactitol assay 99.9%, enthalpy 169.4±0.5 J/g) was milled with a small laboratory hammer mill (Culatti). The feed rate was 10 g/min and the hammer speed 600 rpm. Fine lactitol particles were obtained.

The milled lactitol particles were still in the anhydrous β form according to DSC measurements and X-ray powder diffractograms.

Example 13
Crystallization of β Lactitol by Cooling Crystallization

Lactitol product crystallization run-off (RDS 49.1%, purity about 94%) was used as feed solution. The solution was evaporated under reduced pressure to RDS 93.2%. The syrup was further concentrated by boiling without vacuum until the temperature 133° C. was reached. The syrup (2.9 kg, RDS 95%) was moved to a reaction vessel.

Seeding was made by 1 g milled anhydrous α lactitol (lot N050 32701 manufactured by Xyrofin Oy, Kotka) at 120° C. The mass was cooled from 120° C. to 100° C. linearly during 2 hours. The obtained crystals were typically needle-like in shape indicative of orthorhombic anhydrous β lactitol.

The mass was centrifuged using a laboratory centrifuge after 18 hours from seeding.

Centrifugation parameters: 3500 rpm for 1 minute with hot 20 ml 85° C. water wash. The slightly yellowish crystals were dried over night at 80° C. oven.

Example 14
Crystallization of β Lactitol by Cooling Crystallization

Lactitol product crystallization run-off (RDS 49.1%, purity about 94%) was used as feed solution. The solution was evaporated under reduced pressure to RDS 84.6%. The syrup was further concentrated by boiling without vacuum until the temperature 129° C. was reached. The syrup (RDS 91.6%) was moved to a reaction vessel. Seeding was made at 105° C. by 1 g milled anhydrous α lactitol (lot N050 32701) manufactured by Xyrofin Oy, Kotka, Finland). The mass was cooled from 105° C. to 85° C. linearly during 2 hours. The crystals were seen to have the typical elongated shape indicative of anhydrous β lactitol.

The mass was centrifuged using a laboratory centrifuge after 18 hours from seeding. Centrifugation parameters: 3500 rpm for 1 minute with hot 20 ml 85° C. water wash. The white crystals were dried over night at 80° C. oven.

Example 15
Short Dough Biscuit

Orthorhombic anhydrous β lactitol was produced in accordance with Example 4 and dried. The crystals were milled to a mean particle size under 312μ. Milled lactitol CM50 (produced by Danisco Sweeteners), which has previously proven to give a biscuit with good eating qualities, was used as a control.

| Ingredients | % Fresh Basis |
| --- | --- |
| Wheat flour | 48.7 |
| Lactitol, milled | 20.6 |
| Butter | 17.6 |
| Water | 9.3 |
| Skimmed milk powder | 2.1 |
| Salt | 0.6 |
| Malt extract | 0.9 |
| Sodium bicarbonate | 0.2 |
| Acesulfame K | q.s. |
| Butter flavour | q.s. |

PROCEDURE
1. Combine dry ingredients with the butter and mix together.
2. Add malt extract and butter flavour to water and gradually stir into mixture.
3. Beat thoroughly.
4. Roll to a sheet, approximately 5 mm thick and cut biscuits as required.
5. Bake at 140° C. for approximately 20 minutes.

There were no problems in the preparation or baking of either one of the samples. The biscuits were golden, firm and had a good snap and crunch.

Example 16
High Ratio Madeira Cake

Orthorhombic anhydrous β lactitol was produced in accordance with Example 4 and dried. The anhydrous β lactitol crystals had a particle size under 800μ. As a control crystalline lactitol monohydrate (produced by Danisco Sweeteners) was used.

| Ingredients | % Fresh Basis |
| --- | --- |
| High ratio cake flour | 22.5 |
| Lactitol, crystalline | 20.7 |
| Polydextrose, Litesse II (Danisco Sweeteners) | 5.2 |
| Egg, fresh whole | 18.0 |
| High ratio fat | 13.5 |
| Skimmed milk powder | 1.6 |
| Baking powder | 0.9 |
| Salt | 0.6 |
| Spray dried egg albumen powder | 1.1 |
| Acesulfame K | 15.7 |

PROCEDURE
1. Place all liquids in a Hobart bowl, followed by the dry ingredients and the fat.
2. Mix on speed 1 for 30 seconds. Scrape down.
3. Mix on speed 2 for 1½ minutes. Scrape down.
4. Mix on speed 2 for a further 1½ minutes or until a relative density of 0.70–0.75.
5. Deposit 300 g into paper cases into 1 lb cake tins.
6. Cook in a pre-heated oven at 200° C. for 30 minutes.

When making the high ratio madeira cakes, better relative density and baked loss were measured using the anhydrous crystals of the present invention. The β cake looked very similar to the control although the surface was sticky, unlike the control. The crumb structure was more fragile than the control and the cake was softer eating. The cake was acceptable.

Example 17
Cream Filling

The lactitol grade used for this application was anhydrous β lactitol having a particle size under 250μ. As a control commercially available milled lactitol was used.

| Ingredients | % Fresh Basis |
| --- | --- |
| HPKO (Arkdy Craig Miller) | 29.0 |
| Lactitol, L050 (Danisco Sweeteners) or | 60.0 |
| β lactitol | 60.0 |
| Skimmed milk powder | 10.4 |
| Emulsifier, Lecithin | 0.2 |
| Colour, Beta Carotene (Warner Jenkinson 801001) | 0.2 |
| Flavour (Bush Boske Allen Creamy Vanilla D4806) | 0.2 |

PROCEDURE
1. Melt the HPKO.
2. Add to the remaining ingredients in a Hobart bowl. Mix together on speed 2 for 5 minutes using the whisk attachment.

There were no problems in the preparation of the samples. Both creams were smooth and had good spreadability.

Example 18
Milk Chocolate

| Preparation of milk chocolate ingredients | |
| --- | --- |
| Lactitol (crystalline anhydrous β) | 420 g |
| Cocoa butter | 272 g |
| Cocoa mass | 143 g |

-continued

Preparation of milk chocolate ingredients

| Milk powder | 142 g |
|---|---|
| Lecithin | 5.0 g |
| Vanillin | 0.2 g |
| Polydextrose (Litesse II) | 18.0 g |

The lactitol, cocoa mass, milk powder, salt, vanillin and part of the cocoa butter were mixed to a homogeneous paste in a Stephen mixer at 30–40° C. The particle size of the mass was comminuted in a Lehmann three roller refiner, the rolling pressures being 100 final mixing, i.e. conching of the chocolate mass was carried out in a conche at 60° C. for 18 hours with a speed of 4.5. The lecithin was mixed at the end of the conching step.

The sample was then stored molten at 50° C. for a period of 7 days. The viscosity of the conched chocolate mass was measured (Haake RV 20 Viscometer) and the yield value was calculated. No thickening was observed. Performance was comparable to anhydrous lactitol α and superior to lactitol monohydrate and lactitol dihydrate where thickening would be apparent. The viscosity and yield values have been presented in Table 3 below.

TABLE 3

Viscosity and yield value of milk chocolate masses after storing at 50° C.

| Time hours | Viscosity Pas | Yield value Pa |
|---|---|---|
| 0 | 0.8467 | 2.093 |
| 24 | 0.7416 | 3.092 |
| 48 | 0.7906 | 2.625 |
| 144 | 0.7971 | 2.559 |
| 168 | 0.7490 | 2.746 |

On account of its lower viscosity, chocolate mass manufactured using crystalline anhydrous β lactitol was easier to treat further into products than lactitol monohydrate or dihydrate masses.

In the present specification the novel anhydrous β lactitol has been described with reference to data analyzed from crystal samples obtained by various processes. It is well understood by those skilled in the art that the physical characteristics of the crystals may very slightly with the production conditions and that, therefore, the present application should be taken to concern the novel crystal species in any of its identifiable forms irrespective of whether the numerical values presented in the specification are exactly met or not. It is also clear that the present invention concerns any normal processes for producing the crystals and that many variations to the processes described in detail in the present application are obvious to those skilled in the art and hence encompassed by the scope of the appended claims.

What is claimed is:

1. A process for preparing anhydrous lactitol crystals belonging to the orthorhombic $P2_12_12_1$ crystal system and having unit cell constants about a=9.6 Å, b=11.1 Å, c=14.0 Å, by crystallizing from an aqueous solution which contains not less than 70%, of lactitol on dry matter, characterized by bringing said aqueous lactitol solution to supersaturation in regard to lactitol, and subjecting the solution to crystallization conditions at a temperature between 70 and 150° C. by boiling and/or cooling crystallization, allowing said solution to crystallize until a substantial first crystal yield is obtained, and conditioning said first crystal yield at a temperature of 70–100° C. for a sufficient time to allow said first crystal yield to convert into a second crystal yield comprising said orthorhombic anhydrous lactitol crystals, recovering said orthorhombic anhydrous lactitol crystals from the mother liquor, and optionally washing and drying said crystals.

2. A process according to claim 1, characterized in that said crystallization is performed with spontaneous nucleation or with seeding with seeds of crystalline lactitol, and that said first crystal yield comprises monoclinic anhydrous lactitol.

3. A process according to claim 1 or 2, characterized in that said crystallization is performed by cooling said lactitol solution from a starting temperature of about 100–80° C. to an end temperature of about 70–80° C. and conditioning said first crystal yield at said end temperature.

4. A process according to claim 2 characterized in that a mixture containing orthorhombic anhydrous lactitol and monoclinic anhydrous lactitol is recovered.

5. A process for preparing anhydrous lactitol crystals belonging to the orthorhombic $P2_12_12_1$ crystal system and having unit cell constants about a=9.6 Å, b=11.1 Å, c=14.0 Å, by crystallizing from an aqueous solution which contains not less than 70%; of lactitol on dry matter, characterized by bringing said aqueous lactitol solution to supersaturation in regard to lactitol, and subjecting the solution to crystallization conditions at a temperature between 70 and 150° C. by boiling and/or cooling crystallization, seeding said supersaturated solution with seed crystals of orthorhombic anhydrous lactitol and separating the resulting orthorhombic anhydrous lactitol crystals from the mother liquor, and optionally washing and drying, the resulting orthorhombic anhydrous lactitol crystals being anhydrous lactitol crystals belonging to the orthorhombic $P2_12_12_1$ crystal system and having unit cell constants about a=9.6 Å, b=11.1 Å, c=14.0 Å.

6. A process according to claim 5, comprising
   (a) evaporating an aqueous solution of lactitol to a concentration of 80–95% by weight and to make a supersaturated solution;
   (b) seeding the supersaturated solution at a temperature within the range 120–80° C.;
   (c) optionally evaporating further while adding lactitol solution within said temperature range to increase the crystal content;
   (d) cooling the resulting mixture;
   (e) separating the orthorhombic anhydrous lactitol crystals from the mother liquor; and
   (f) washing and drying said crystals.

7. A process according to claim 5 or 6, wherein said crystals are provided in a crystal foot of orthorhombic anhydrous lactitol.

8. A process for preparing anhydrous lactitol crystals belonging to the orthorhombic $P2_12_12_1$ crystal system and having unit cell constants about a=9.6 Å, b=11.1 Å, c=14.0 Å, by crystallizing from an aqueous solution which contains not less than 70%, of lactitol on dry matter, characterized by bringing said aqueous lactitol solution to supersaturation in regard to lactitol, and subjecting said solution to slow crystallization conditions at a temperature between 150 and 70° C. by slow boiling and/or cooling crystallization, recovering said orthorhombic anhydrous lactitol crystals from the mother liquor, and optionally washing and drying said crystals.

9. A process according to claim 8, characterized by evaporating an aqueous solution of lactitol to a concentration of 85–95% by weight and seeding the supersaturated solution by adding seed crystals of monoclinic and/or orthorhombic anhydrous lactitol in a temperature range 80–100° C., and cooling the mixture slowly to an end temperature ranging from 70° C. to 90° C., and recovering the resulting orthorhombic anhydrous lactitol crystals from the mother liquor.

10. A process according to claim 9, characterized by additionally conditioning the crystal yield at said end temperature prior to recovering said crystals.

11. A process according to any one of the preceding claim 1, 5, or 8 characterized in that the crystallization of orthorhombic anhydrous lactitol is improved by one or more measures selected from the addition of accelerating impurities such as lactulitol to the aqueous solution of lactitol, the increase of supersaturation of said solution, the prolonging of the crystallization and/or conditioning time, and the addition of seed crystals of orthorhombic anhydrous lactitol ($\beta$) to said solution.

12. The process according to claim 2 wherein seeds of monoclinic anhydrous lactitol is utilized in said crystallization.

13. A process according to claim 11 characterized in that a mixture containing orthorhombic anhydrous lactitol and monoclinic anhydrous lactitol is recovered.

14. The process according to claim 13 wherein in step (d) the mixture is cooled to a temperature of 70–80° C.

* * * * *